(12) United States Patent
Byrd et al.

(10) Patent No.: US 9,023,105 B2
(45) Date of Patent: May 5, 2015

(54) EAR MOLDING DEVICE FOR CORRECTING MISSHAPED EARS

(71) Applicant: Henry Stephenson Byrd, Terrell, TX (US)

(72) Inventors: Henry Stephenson Byrd, Terrell, TX (US); C. Kenneth French, Cranfills Gap, TX (US); Garrett Barker, Meridian, TX (US)

( * ) Notice: Subject to any disclaimer, the term of this patent is extended or adjusted under 35 U.S.C. 154(b) by 0 days.

(21) Appl. No.: 14/477,707

(22) Filed: Sep. 4, 2014

(65) Prior Publication Data
US 2014/0378879 A1    Dec. 25, 2014

Related U.S. Application Data

(62) Division of application No. 13/434,465, filed on Mar. 29, 2012, now Pat. No. 8,852,277, which is a division of application No. 12/368,765, filed on Feb. 10, 2009, now Pat. No. 8,167,942.

(51) Int. Cl.
| A61F 5/01 | (2006.01) |
| A61F 11/00 | (2006.01) |
| A61B 19/00 | (2006.01) |
| A61B 17/00 | (2006.01) |

(52) U.S. Cl.
CPC .............. *A61F 5/0102* (2013.01); *A61F 11/00* (2013.01); *A61F 11/006* (2013.01); *A61B 19/24* (2013.01); *A61B 2017/00787* (2013.01); *A61F 11/004* (2013.01)

(58) Field of Classification Search
CPC ....... A61F 11/00; A61F 11/004; A61F 11/06; A61F 11/14; A61F 5/0102; A61B 2017/00787

USPC ............................................................ 623/10
See application file for complete search history.

(56) References Cited

U.S. PATENT DOCUMENTS

| 2,339,572 A | 1/1944 | Ludwig |
| 3,823,713 A | 7/1974 | Shah |
| 4,187,838 A | 2/1980 | Dubrowski |
| 5,295,950 A | 3/1994 | Godley |
| 5,433,748 A | 7/1995 | Wellisz |
| 5,615,417 A | 4/1997 | Jackson |
| 5,827,212 A | 10/1998 | Gaskill |
| 6,517,557 B1 | 2/2003 | Sorribes |

(Continued)

FOREIGN PATENT DOCUMENTS

WO    WO2009/014908 A1    1/2009

OTHER PUBLICATIONS

PCT/US08/069658 International Search Report and Written Opinion, PCT, Oct. 1, 2008.

(Continued)

*Primary Examiner* — David Isabella
*Assistant Examiner* — Suba Ganesan
(74) *Attorney, Agent, or Firm* — Fish & Richardson P.C.

(57) ABSTRACT

A system and method for correcting misshaped ears using a molding device having one or more braces supporting a scaphal mold. The one or more braces and the scaphal mold are adapted to retain the helix and the helical rim of a misshaped ear within a space defined between the one or more braces and the scaphal mold, and to maintain a substantially correct anatomical shape of the helix and the helical rim.

3 Claims, 8 Drawing Sheets

(56) References Cited

U.S. PATENT DOCUMENTS

| | | | |
|---|---|---|---|
| 7,093,600 | B2 | 8/2006 | Sorribes |
| 7,117,546 | B2 | 10/2006 | Goulding |
| 7,799,075 | B2 | 9/2010 | Kang et al. |
| 2004/0237175 | A1 | 12/2004 | Carrafield et al. |
| 2006/0184184 | A1 | 8/2006 | Sorribes |
| 2008/0086067 | A1 | 4/2008 | Hay et al. |

OTHER PUBLICATIONS

N. Kurozumi, et al., "Non-surgical correction of a congenital lop ear deformity by splinting with Reston foam," British Journal of Plastic Surgery, 1982, 35, 181-182.

Kiyoshi Matsuo, M.D.., et al., "Nonsurgical Correction of Congenital Auricular Deformities," Clinics in Plastic Surgery, Apr. 1990, vol. 17, No. 2.

Yehuda Ullmann, M.D., et al., "Early Nonsurgical Correction of Congenital Auricular Deformities," Plastic and Reconstructive Surgery, Mar. 2002, vol. 109, No. 3, pp. 907-913.

Takatoshi Yotsuyanagi, M.D., Ph.D., "Nonsurgical Correction of Congenital Auricular Deformities in Children Older than Early Neonates," Plastic and Reconstructive Surgery, Jul. 2004, vol. 114, No. 1, pp. 190-191.

Ear Buddies™ Splints—How to fit Ear Buddies Splints, retrieved Nov. 11, 2008 from the internet. <URL: http://www.earbuddies.co.uk/pws/Content.ice?page=FIT&pgForward=content>, p. 1-6.

AuriClinic, Prominent ears treatment, retrieved Nov. 11, 2008 from the internet. <URL:http://www.auriclinic.com/clinic/prominenet-ears-treatment/patented-method/.

AuriClinic, FAQ, retrieved Nov. 11, 2008 from the internet. <URL:http://www.auriclinic.com/clinic/faq, p. 1-5.

Swee Tan, et al., "Correction of deformational auricular anomalies by moulding-results of a fast-track service," The New Zealand Medical Journal, Sep. 2003.

Jou Hyun Park, M.D., et al. "Non-Operative Correction of Congenital Auricular Deformities Using a Silicone Splint," National Library of Medicine, Sep. 2000, vol. 27, No. 5, pp. 532-538.

D J M MacDonald, et al., "Case presentation: a novel way of treating acute cauliflower ear in a professional rugby player," B J Sports Med, 2005. <URL:http://www.bjsportmed.com >.

Michael Miravet Sorribes, M.D., et al. "NonSurgical Treatm ent of Prominent Ears With the Auri Method," Arch Otolaryngol Head Neck Surg, Dec. 2002, vol. 128, pp. 1369-1376.

Swee T. Tan, MBBS, et al. "Molding Therapy for Infants with Deformation Auricular Anomalies," Annals of Plastic Surgery, Mar. 1997, vol. 38, No. 3, 8 pages.

S. T. Tan et al. "A Split for Correction of Congenital ear Deformities," British Journal of Plastic Surgery, Apr. 1994, vol. 47, No. 8, pp. 575-578.

J. Oroz, et al., "Congenital anomalies of the auricle: correction using external splints," European Journal of Plastic Surgery, 1995, vol. 18, pp. 288-292.

F. Schonauer, et al., "Splintage for correction of congenital ear deformities," European Journal of Plastic Surgery, Sep. 2003, vol. 26, pp. 290-293.

K. Matsuo, et al. "A Splint for Nonsurgical Correction of Cryptotia," European Journal of Plastic Surgery, 1989, vol. 12, pp. 186-187.

K. Matsuo, et al. "Nonsurgical Correction of Congenital Auricular Deformaties in the Early Neonate: A Preliminary Report," Plastic and Reconstructive Surgery, 1984, vol. 73, pp. 38-50.

International Preliminary Report on Patentability issued in International Application No. PCT/US2008/069658, Jan. 26, 2010, 8 pages.

International Search Report and Written Opinion of the International Searching Authority issued in International Application No. PCT/US2009/036328, Feb. 23, 2010, 14 pages.

PCT/US2009/036328 International Preliminary Report on Patentability, PCT, Aug. 25, 2011, 8 pages.

Office Action issued in Chinese Patent Application No. 200880108740.X dated May 11, 2011, 13 pages.

Communication pursuant to Article 94(3) EPC issued in international application No. 08 781 618.7-2310, Aug. 12, 2010, 6 pages.

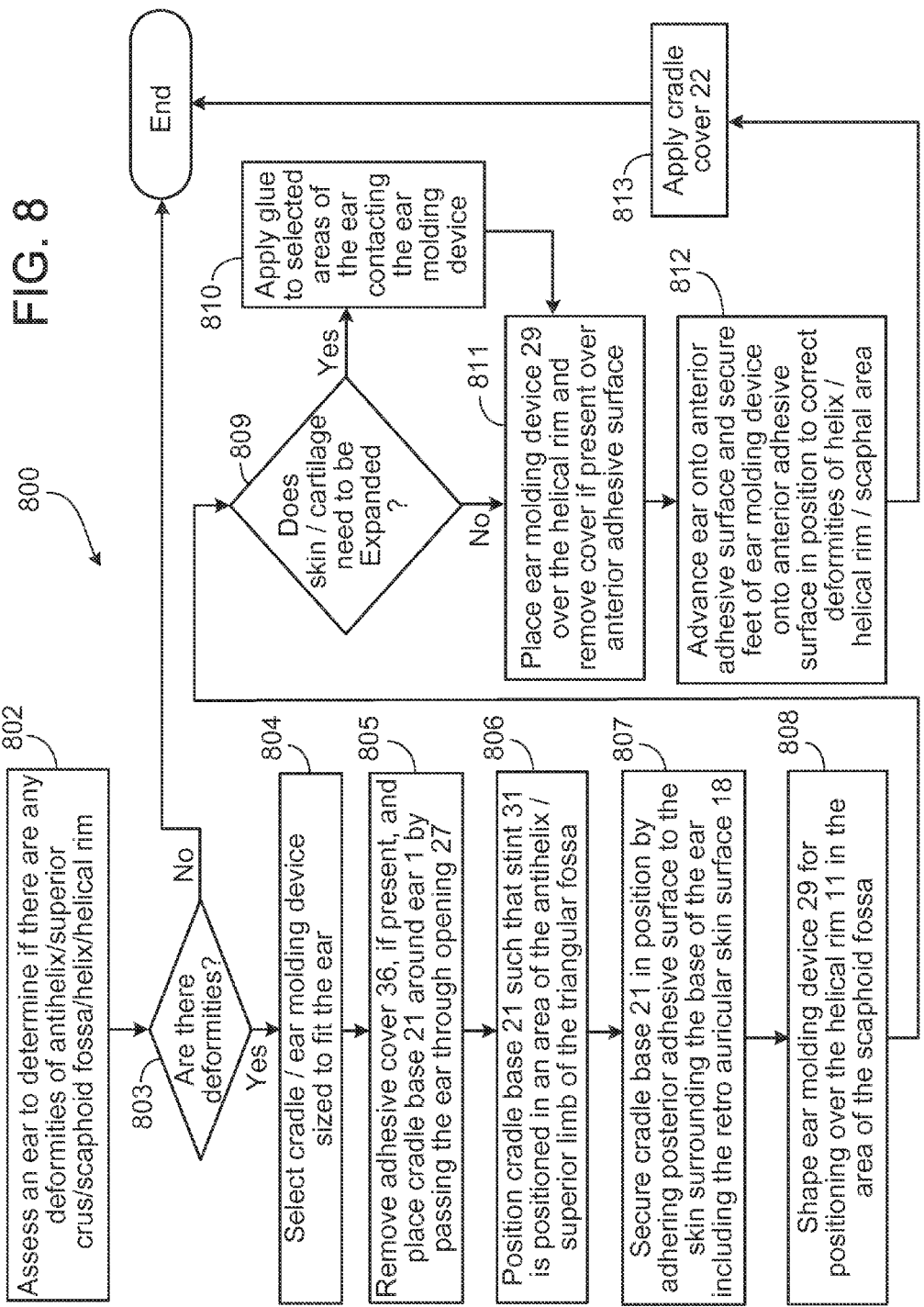

EAR MOLDING DEVICE FOR CORRECTING MISSHAPED EARS

CROSS-REFERENCE TO RELATED APPLICATION

This application is a divisional application of U.S. application Ser. No. 13/434,465 filed on Mar. 29, 2012, which is a divisional of and claims priority under 35 U.S.C. §121 to U.S. application Ser. No. 12/368,765, filed Feb. 10, 2009, the entire content of which is hereby incorporated by reference.

TECHNICAL FIELD

This invention relates to correcting misshaped ears, and more particularly to non-surgical correction of misshaped ears.

BACKGROUND

The ear consists of a complex arrangement of cartilage covered by skin, forming the characteristic shape of the ear (See FIG. 1). Some of the major structures of the ear are the helix, which is the outer most part of the ear and is characterized by a roll or rim (helical rim). The scapha (or scaphoid fossa) separates the helical rim from the antihelix which forms a defining curvature separating the scapha from the concha. The antihelix gives rise to a Y shaped structure having two crura. The two crura form the fork of the Y and merge into the body of the antihelix. The area between the two crura is the triangular fossa. The deep recess leading to the auditory canal is the conchal bowl. It has an oblique and vertical component. The vertical component contributes to ear projection and is continuous with the antihelix.

Depending on the survey, there may be an incidence of misshapen or deformed ears in the newborn population of up to or greater than forty percent. A few among the various types of congenital auricular deformities are prominent ear, cup ear, lop ear, Stahl's ear, conchal crus, misshapen ears, helical rim compression, and Tanzer I-II constricted ear.

Prominent ear is an ear in which the helical rim projects more than 15-18 mm from the mastoid in an adult and more than 5 mm in an infant. Cup ear is characterized by incomplete curvature or formation of the antihelix and superior limb of the triangular fossa, and without the normal curve of these structures, the ear "cups" forward. Lop ear is characterized by a "lidding" or folding over of the superior third of the ear. Stahl's ear, also called "Spock" ear, is characterized by a "transverse crus" extending off the Y of the antihelix, deforming the natural curve of the helical rim and causing the ear to have a point like an elf's ear. Conchal crus is an abnormal crus or fold that extends across the oblique portion of the conchal floor to the vertical conchal wall, appearing to divide the ear in half at the level of the external auditory canal.

Misshapen ears are variations of malformations of the auricular cartilage that do not fit into the above defined categories. These ears may appear to be "crinkled", folded, or collapsed in varying parts of the framework. Helical rim compression is characterized by an inward buckling of the rim disturbing its normal curvilinear contour. Tanzer I-II constricted ears have increasingly severe grades of skin and/or cartilage absence or deficiency. In Tanzer I ears, the helical rim is rolled-in as there is a shortage or deficiency of skin along the inner rim that prevents the helical rim from being rolled out. With Tanzer II, the deficiency is greater and actually affects the scaphal cartilage as well. Both surgical and non-surgical means have been used in an attempt to correct these and other deformities of the ear.

SUMMARY

Techniques are described for non-surgical correction of misshapen ears. Although various types of misshaped ears present at birth may involve deformities of one or more anatomic structures of the ear, the techniques presented below can be tailored to correct deformities of the one or more anatomic structures. Some of the anatomic structures of the ear of interest are an antihelix, a superior limb of the triangular fossa, a helical rim, a concha, a base, and a scaphal area.

In one general aspect, a molding device for a human ear has one or more braces, and a scaphal mold supported by the one or more braces. The one or more braces and the scaphal mold are adapted to retain the helix and helical rim within a space defined between the one or more braces and the scaphal mold and to maintain a substantially correct anatomical shape of the helix and the helical rim.

In another general aspect, a molding system for the human ear has a cradle including a base section and a cover. The base section defines an opening dimensioned to accommodate the passage of the ear through the opening. The base section has a posterior surface and an anterior surface. The cover is releasably engageable with the base section. When engaged with the base section, the cover defines a compartment between an inner surface of the cover and an inner surface of the base section. The molding system for the ear also has an ear molding device, including one or more braces and a scaphal mold supported by the one or more braces. The one or more braces and the scaphal mold are adapted to retain the helix and the helical rim within a space defined between the one or more braces and the scaphal mold, and to maintain a substantially correct anatomical shape of the helix and the helical rim.

In another general aspect, a method of correcting a misshaped ear includes placing a cradle base over the ear. The cradle base includes an anterior surface, a posterior surface, and an opening dimensioned to accommodate passage of the ear. The cradle base is releasably engageable with a cradle cover to define a compartment between an inner surface of the cover and the anterior surface of the base, such that the ear can be positioned within the compartment. The method includes locating a splint on the anterior surface, such that the splint is arranged on the anterior surface in a position substantially corresponding to an area of the antihelix and the superior limb of the triangular fossa. The method includes placing a posterior surface of the ear between the base of the ear and the helical rim over the splint, such that the splint maintains a substantially correct anatomical configuration of the ear in the area of the antihelix and the superior limb of the triangular fossa. The method includes retaining the helix in a space defined between a scaphal mold and one or more braces supporting the scaphal mold, such that the scaphal mold maintains a substantially correct anatomical configuration of the scaphal area of the ear.

Implementations may include one or more of the following features. Each of the one or more braces can include a foot member positioned at an end of each brace distal to the scaphal mold. The foot member is adapted to facilitate maintaining the substantially correct anatomical shape of the helix. A surface of the one or more braces facing the scaphal mold can define a substantially correct anatomic curvature for the helix. The foot can include a broad flat surface adapted for securing the ear molding device to a first surface. The one or more braces can include a vertical support surface adapted to reversibly engage a second surface. The one or more braces can include a horizontal support surface adapted to reversibly engage a third surface. The vertical and horizontal support surfaces when engaged to the second and third surfaces, respectively, can stabilize the ear molding device.

The one or more braces each can have an adjustable malleable support adapted to retain an adjusted configuration of the brace. The scaphal mold can include a generally arc-shaped semi-cylindrical extension from the one or more braces having rounded edges. The extension can be adapted to maintain a substantially correct anatomical shape of the scaphal area of the ear. The scaphal mold can include an adjustable malleable retainer located in an axis parallel to the arc of the scaphal mold. The retainer can be adapted to retain an adjusted configuration of the scaphal mold.

An adhesive backing can be dimensioned to fit the posterior surface of the base section and can define an opening corresponding to the opening in the base section. The adhesive backing can include an anterior adhesive surface adapted to adhere the posterior surface of the base section, and a posterior adhesive surface adapted to adhere to a periauricular skin surface. The base section can define a second opening posterior to the opening, such that a strip of the anterior surface separates the opening from the second opening. A first stent can be arranged on the anterior surface and can be adapted to maintain a substantially correct anatomical shape of the ear in an area of the antihelix and the superior limb of the triangular fossa. The strip of the anterior surface can be adapted to be broken when the cradle is separated from the backing.

Each foot can include a broad flat surface adapted for securing the ear molding device to a portion of the anterior adhesive surface exposed by the second opening. The base section and the cover can include a vertical wall. A strip of double sided adhesive can be positioned on the vertical wall. The one or more braces have a vertical support surface adapted to reversibly engage the double sided adhesive positioned on the vertical wall. The one or more braces can have a horizontal support surface adapted to reversibly engage the cover when the cover is engaged with the base section. The vertical and horizontal support surfaces when engaged to the vertical wall and the cover, respectively, stabilize the ear molding device. The one or more braces can be secured to the anterior surface. The cradle cover can be engaged with the cradle base. A kit can contain one or more cradles, one or more ear molding devices, and one or more adhesive backings.

DESCRIPTION OF DRAWINGS

FIG. 8 is a flow chart for treating deformities of an ear with a system for correcting misshaped ears.

Like reference symbols in the various drawings indicate like elements.

DETAILED DESCRIPTION

Figure 1:
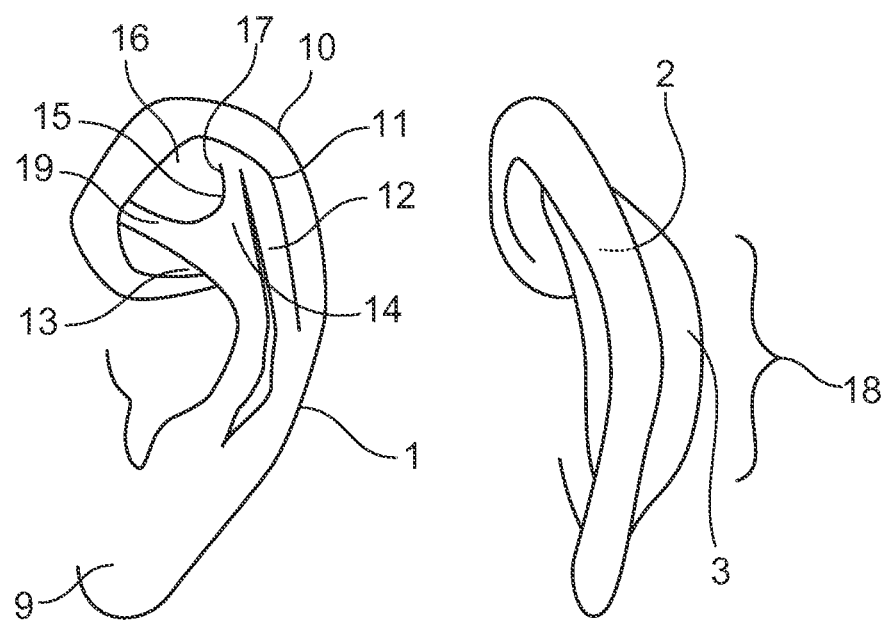
FIG. 1 is an anatomical drawing of an ear showing the major structures of the ear.

As shown in FIG. 1, an ear 1 has a complicated structure, composed of cartilage covered by skin. Deformities involving various structures of the ear occur causing the ear to appear misshaped. The following structures are some of the structures of interest when discussing misshaped ears. Progressing generally from peripheral to central regions of the ear, the structures of interest are a helix 10, having a helical rim 11. A scaphoid fossa (scapha) 12 is located between the helical rim 11 and an antihelix 14. The antihelix 14 has a crura 15 forming a superior limb (superior crus) 17 and an inferior limb (inferior crus) 19 of a triangular fossa 16. A concha 13 is located in an area inferior to the inferior limb of the triangular fossa. An ear lobe 9 hangs down from the ear, inferiorly. A retroauricular skin surface 18 can be seen from a posterior view as extending from the base of the ear. A posterior aspect or skin surface 2 of the ear generally extending from the base of the ear towards the helix is also depicted in the posterior view of the ear.

Abnormalities of one or more of these structures result in ear deformities, such as prominent ear, cup ear, lop ear, Stahl's ear, conchal crus, misshapen ears, helical rim compression, lidding, and Tanzer I and II constricted ear. A non-surgical approach to the correction of these and other deformities of the ear can be accomplished using one or more of the components of a system for correcting misshaped ears described in co-pending U.S. application Ser. No. 12/113,452, filed May 1, 2008, the contents of which are incorporated by reference herein in its entirety.

Figure 2:
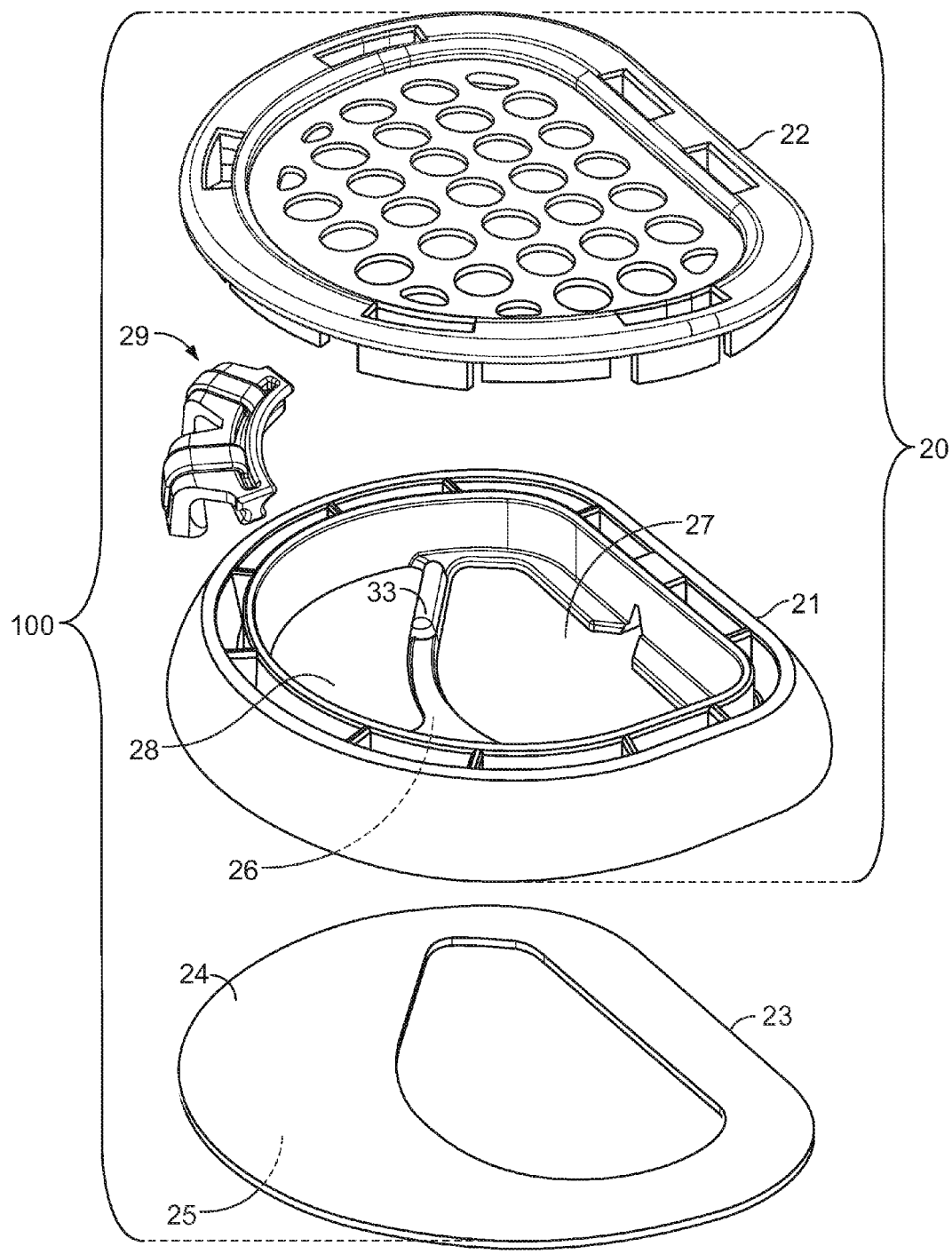
FIG. 2 is an exploded view of a system for correcting misshaped ears including a ear cradle with a base, a cover, an adhesive backing, and an ear molding device configured to shape an ear in an area of the helix, helical rim, and scaphoid fossa.

Referring to FIG. 2, an exploded view of system 100 for correcting a misshaped ear is illustrated. System 100 can be used to correct deformities of one or more of above structures of the ear by molding or shaping the ear to create a substantially correct anatomic configuration. The system 100 has a cradle 20 in which the ear is positioned to correct the deformities of the ear. Cradle 20 has a cradle base 21 and a cradle cover 22. The cradle base 21 is releasably engageable with the cradle cover 22 and, when engaged, defines a compartment between the cradle base 21 and the cradle cover 22. The cradle base 21 and the cradle cover 22 are assembled and positioned around the ear, such that the ear fits within the compartment, for the purpose of correcting deformities that cause the ear to be misshaped. The cradle base and cradle cover can be made from biocompatible materials, such as thermoplastics, thermosets, and elastomers (including PVC, polycarbonate, polyurethane, silicone, polypropylene and polyethylene). The cradle base and cradle cover can be provided in a range of sizes designed to fit ears of differing proportions.

Figure 4:
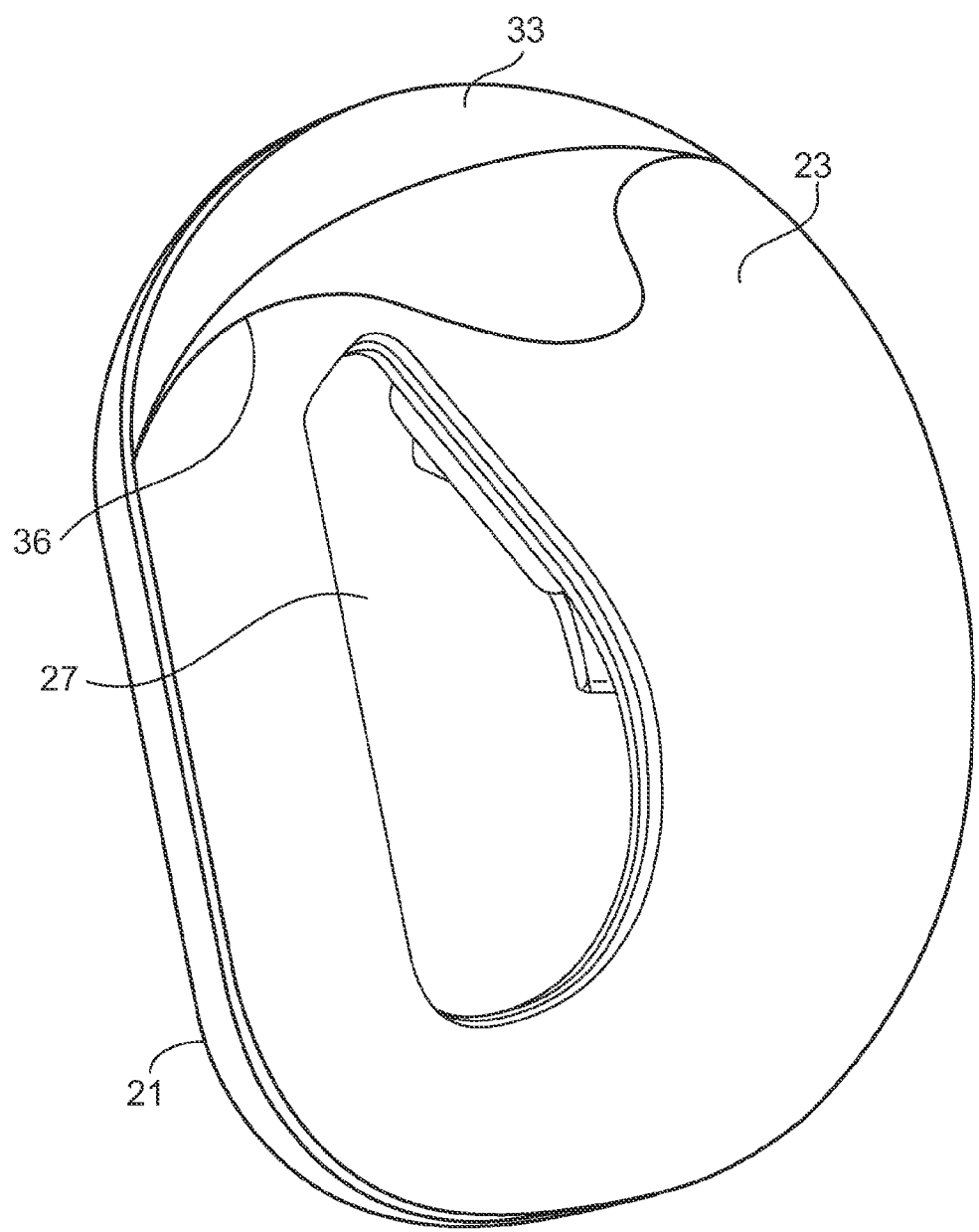
FIG. 4 is a posterior view of a cradle base.

Referring to FIGS. 2 and 4, the cradle base 21 has a posterior surface 26 that includes an opening 27 through which the ear can be positioned within the compartment defined by the base and cover, and a second opening 28. Adhesive backing 23 has an anterior adhesive surface 24 and a posterior adhesive surface 25. Adhesive backing 23 is dimensioned such that the adhesive backing conforms to the shape of the posterior surface of the cradle base 21. The adhesive backing 23 has an opening dimensioned to correspond to the first opening 27 of the cradle base 21. The anterior adhesive surface 24 of adhesive backing 23 can be applied to the posterior surface 26 of the cradle base 21. Once the adhesive backing is applied to the posterior surface of the cradle base, an area of the anterior adhesive surface 24 is exposed by the second opening 28 in the cradle base 21. As seen in FIG. 4, adhesive backing can have a film or protector 36 covering the posterior adhesive surface that can be peeled off when the cradle base is to be secured to the retroauricular skin surface 18. In some implementations, a film or protective layer can cover the anterior adhesive surface exposed by the second opening 28. The adhesive backing can be any biocompatible adhesive backing, such as 3M™ tape products 9917 or 1522.

Ear molding device 29 is configured to be positioned within the compartment defined by the cradle base 21 and cover 22. In some implementations, the ear molding device 29 is adjustably positionable upon an area of exposed anterior adhesive surface of adhesive backing 23 made accessible by the second opening 28. In other implementations, a patch of double-sided adhesive material can be applied directly to the anterior surface 31 of the cradle base 21, such that the ear molding device can be adjustably positioned and adhered directly to the patch of double sided adhesive material. In other implementations, an adhesive can be placed on the ear molding device 29 itself, allowing the ear molding device to be adhered to the anterior surface 31 of the cradle base 21.

Although shown in FIG. 2 as two separate members, in other implementations, the cradle base 21 can be connected to the cradle cover 22 through a flexible or hinged articulation allowing the cradle cover 22 to move from an open position to closed position defining the compartment with the cradle base 21. In some implementations, the cradle base and cradle cover can include holes designed to allow for the passage of air into the compartment and to the skin beneath the cradle base.

The cover 22 can be attached to the base 21 by any reversible attachment mechanism such as two or more snaps, or a hinge and one or more snaps, or hook and loop fasteners, or lug and notch, or a latch type mechanism, or any other type of fastening mechanism that securely and reversibly attaches the cover to the base. The cover can be disengaged from the base at any time by releasing the securing component, i.e., the snaps, the hook and loop fasteners, etc.

Figure 3:
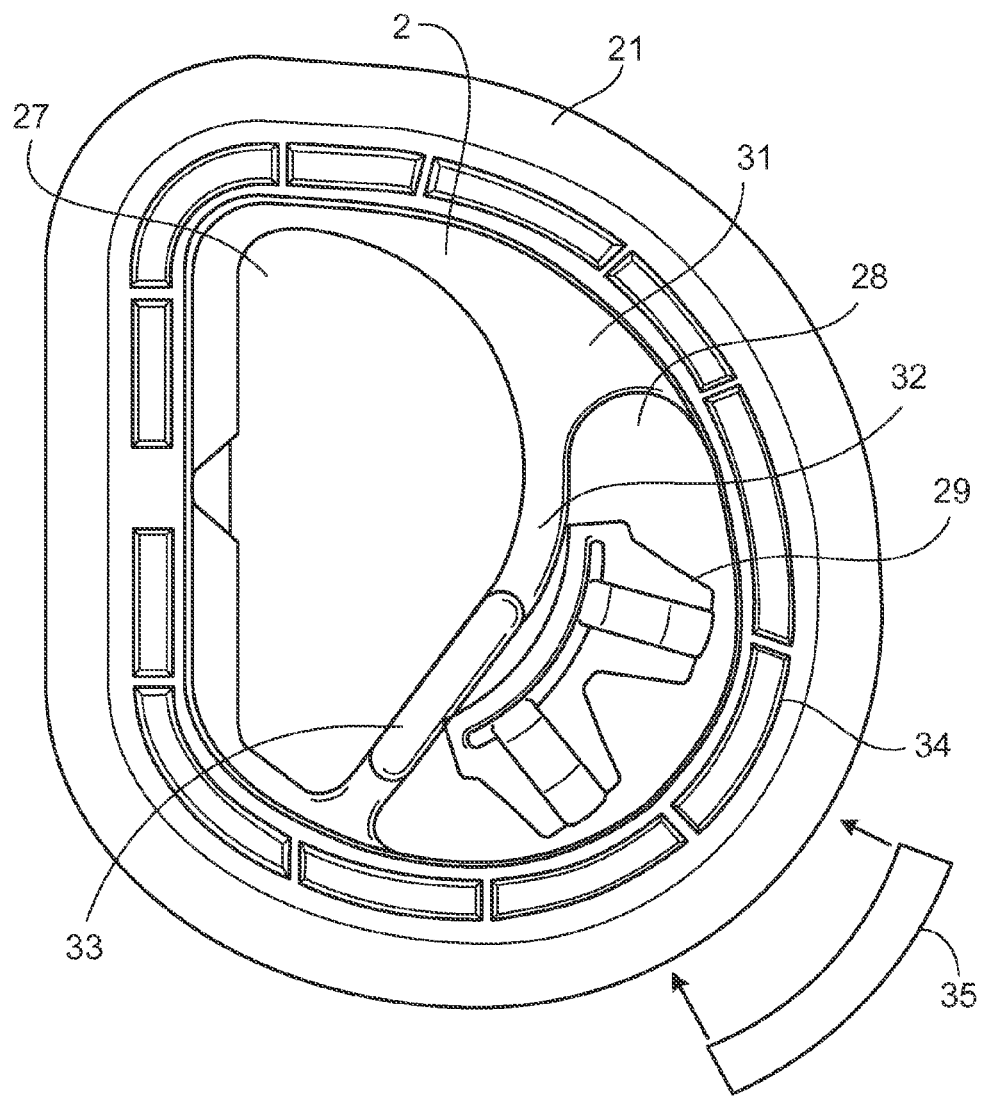
FIG. 3 is a view of a cradle base with an adhesive backing applied to a posterior surface of the cradle base, and an ear molding device applied to an anterior adhesive surface of the adhesive backing.

As shown in FIGS. 2 and 3, base 21 includes a rim (wall) 34 forming the wall of the compartment in which the ear is positioned to correct deformities. Although as shown the majority of the rim or wall 34 of the compartment is formed as part of the base 21, either or both the base 21 and the cover 22 can be dimensioned to form all or part of the rim 34 or wall of the compartment, such that when the base and cover are engaged the wall of the compartment is formed with dimensions configured to accommodate an ear with the deformity to be corrected. The base 21 and cover 22 can be dimensioned to fit ears of different sizes depending on the age and/or size of the patient being treated.

In some implementations, a detachment strip 32 separating the opening 27 from the second opening 28 forms part of the cradle base. The cradle base 21 has an anterior surface 31. A preformed stint (stent/splint) 33 can be positioned on or formed integrally on the anterior surface 31 of the detachment strip 32 of the cradle base 21. The stint 33 can be positioned in an area of the antihelix and the superior limb of the triangular fossa to maintain a substantially correct anatomic shape of the antihelix and the superior limb of the triangular fossa in that region. In other implementations, the cradle base 21 includes opening 27, but does not include opening 28, and the anterior surface extends from opening 27 posterior to the posterior wall of the cradle base 21. The stint 33 can be positioned on a patch of double sided adhesive placed on the anterior surface of the cradle base 21 (or formed on the anterior surface 31), such that the stint 33 can be positioned in an area of the antihelix and the superior limb of the triangular fossa to maintain a substantially correct anatomic shape of the antihelix and the superior limb of the triangular fossa in that region.

In use, the cradle base 21 and the cradle cover 22 are assembled and positioned around the ear 1, such that the base of the ear is positioned in the first opening 27, and the posterior adhesive surface 25 of the adhesive backing can be adhered to the retroauricular (or periauricular) skin surface 18 to maintain the cradle in position about the ear 1.

An area of anterior adhesive surface 24 is exposed by the second opening 28. In some implementations, there is a cover over the anterior adhesive surface that can be removed to expose the anterior adhesive surface. The exposed anterior adhesive surface 24 can be used to tack the skin on the posterior aspect 2 of the ear 1 down after the ear is rolled out over the stint 33, which is positioned in the area where the antihelix and the superior limb of the triangular fossa are to be molded. An ear molding device 29 is positioned over the helical rim in a position to mold the helix, helical rim, and/or the scaphoid fossa, and adhered to the exposed anterior adhesive surface 24. In some implementations, a double adhesive strip 35 (other implementations can use hook and loop fasteners), having adhesive on both sides can be positioned on the inside surface of the wall 34 of the cradle proximate to the position of the ear molding device 29, such that the ear molding device 29 can also be adhered to the inner adhesive surface of adhesive strip 35. In instances where the ear is too small for the ear molding device to be positioned in contact with adhesive strip 35 a shim having adhesive on both sides can be inserted in order to secure the ear molding device 29 to the wall 34, if desired.

Figure 5:
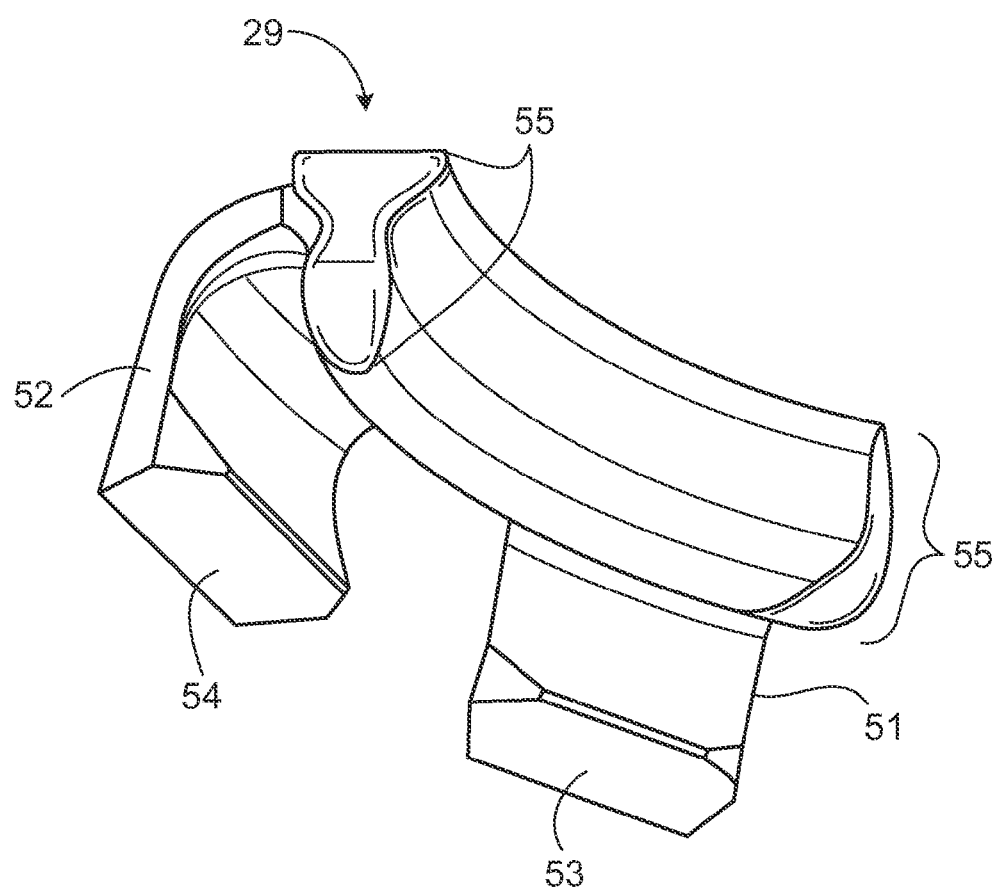
FIG. 5 is a slightly inferior and lateral view of an ear molding device.
Figure 6A:
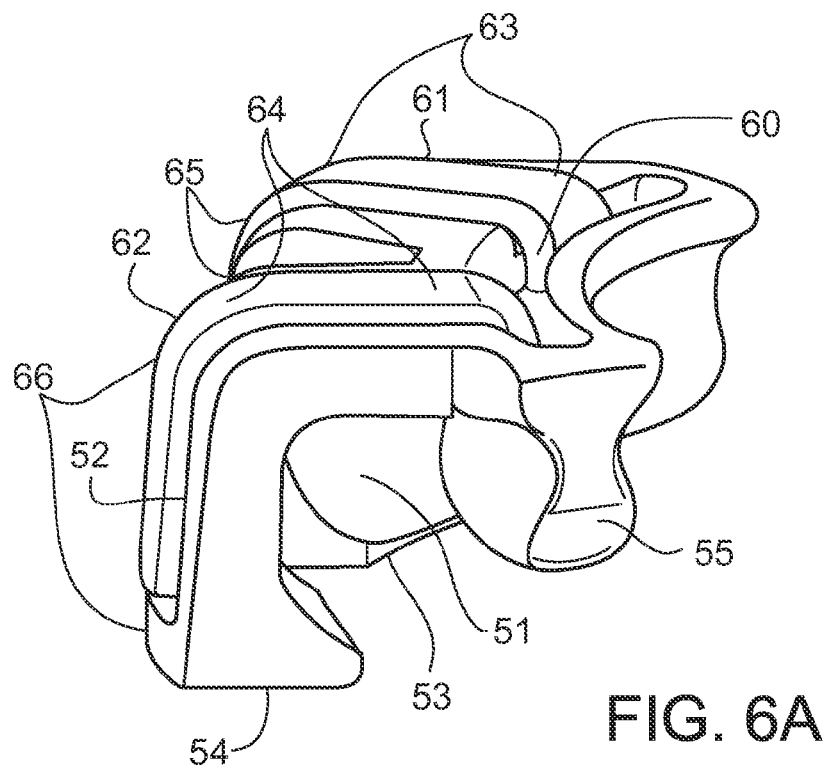
FIG. 6A is a lateral view of an ear molding device.
Figure 6B:
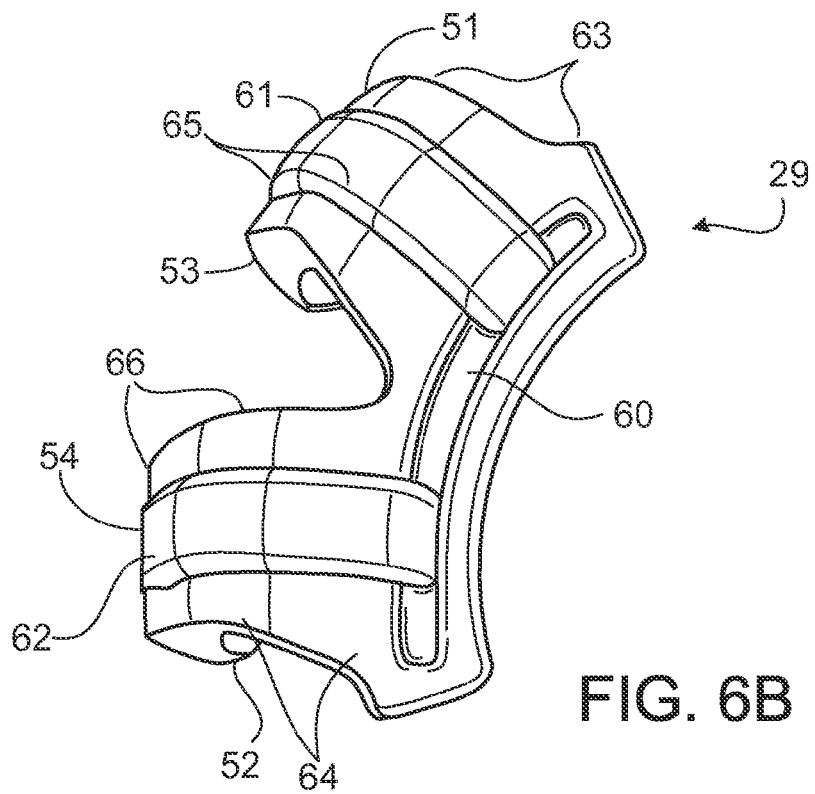
FIG. 6B is a top down view of an ear molding device.
Figure 7:
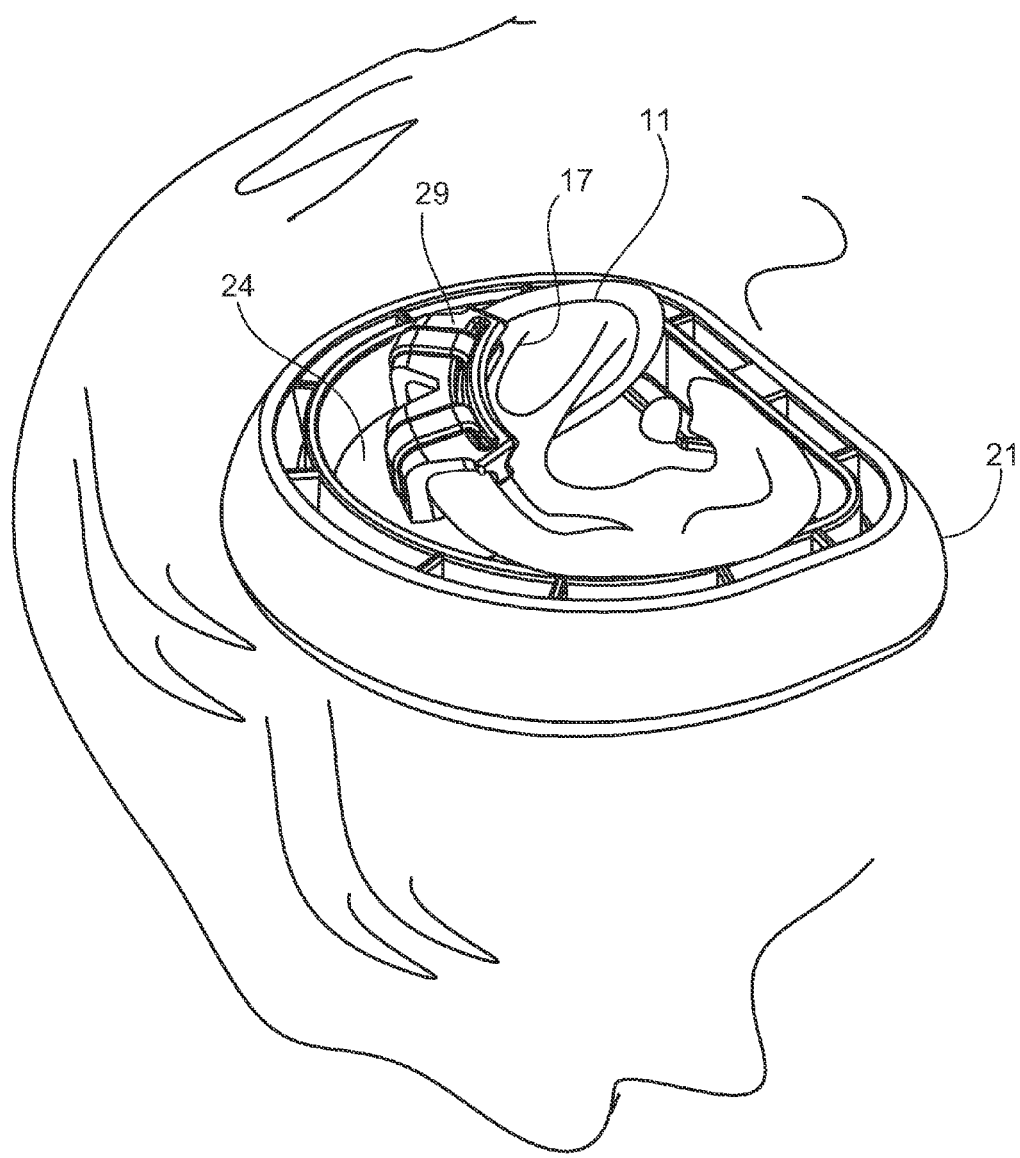
FIG. 7 is a view of a cradle base and an ear molding device positioned around an ear.

As shown in FIGS. 5, 6A and 6B, ear molding device 29 is configured to mold the scaphoid fossa, helix, and the helical rim. In some implementations, the ear molding device 29 can be used expand the skin and cartilage in the area of the helical rim and the scaphoid fossa in addition to molding the shape of the scaphoid fossa, helix, and the helical rim. The ear molding device 29 has a scaphal mold 55 configured to mold the scaphoid fossa into a substantially correct anatomic shape. The exterior surface of the scaphal mold 55 is made from a biocompatible material, such as urethane. Typically, it is desirable to ensure that the scaphal mold 55 is free from sharp or hard edges, preventing the scaphal mold 55 from exerting undue pressure on the skin so as to avoid pressure necrosis of areas of skin in contact with the scaphal mold. The scaphal mold is generally a semi-cylindrical extension from legs (or braces) 51 and 52 having rounded edges and shaped to maintain the substantially correct anatomical shape of the scaphal area 12 of the ear 1. As will be discussed below, the inner curvature of the scaphal mold 55 facing the legs 51 and 52 cooperates with inner surface of legs 51 and 52 to form a space therewith configured to mold the helix and helical rim during their growth while in the ear molding device, such that the growth of the helix and helical rim conforms to a curvature defined by the space between the scaphal mold and the legs.

Leg 51 and leg 52 each have a generally vertical support 65 and 66 and a generally horizontal support 63 and 64, respectively when viewed relative to being positioned on the cradle base. As illustrated, the scaphal mold 55 extends downward from the right and left legs 51 and 52 generally in a direction parallel to the vertical supports 65 and 66. The scaphal mold 55 generally has a rounded edge for contacting the skin in the scaphoid fossa 12 and is generally formed in an arc matching a substantially correct anatomic curvature of the ear in an area of the helical rim where correction of the shape of the helix, helical rim and/or scaphoid fossa is desired. Instead of an arc, other dimensionally similar shapes can be used. Preferably, edges contacting a skin surface that might cause pressure necrosis of the skin should be avoided. As shown in FIG. 6A, the inner curve of the scaphal mold is dimensioned to accommodate the helical rim, while at the same time allowing the scaphal mold to engage an inner surface of the helix, allowing traction to be place on the skin and cartilage of the ear in the area of the scaphoid fossa and the inner surface of the helix, if desired.

Positioned within the scaphal mold 55 is a malleable retainer 60 that can be used to adjust the curvature of the scaphal mold 55 to the substantially correct anatomic shape for the scaphal area 12 of the ear. The scaphal mold 55 is positioned in the scaphoid fossa when correcting a deformity of the scaphoid fossa, helix, and/or the helical rim. Prior to positioning the scaphal mold 55 in the scaphal area 12 of the ear, the curvature of the scaphal mold can be adjusted by bending the malleable retainer 60 to a desired (e.g., substantially correct) anatomic shape. The malleable retainer 60, having an initial shape of an arc, can be constructed to retain a desired curvature as adjusted, thus, maintaining the scaphal mold in a configuration to mold the scaphal area 12 of the ear into a substantially correct anatomic shape.

The ear molding device 29 has a right leg 51 and a left leg 52, having a right foot 53 and left foot 54, respectively. In some implementations, the right leg 51 and left leg 52 are separated by a variable space. In other implementations instead of two legs, the ear molding device can be a single unitary piece having one leg, which can have a second malleable retainer in the foot section to help maintain a desired shape. In other implementations, there may be more than two legs. Legs 51 and 52 can be formed from a biocompatible material such as thermoplastics, thermosets and elastomers (including PVC, silicone, and propylene).

Feet 53 and 54 have a flat surface configured to be positioned on the anterior adhesive surface 24 exposed by the second opening 28, or if there is not second opening 28, then feet 53 and 54 can be positioned either directly onto the anterior surface 31 (by adhesive on each foot), or onto a biocompatible double sided adhesive patch positioned on the anterior surface 31. Feet 53 and 54 are fixedly secured by the adhesive in a position to correct the anatomical deformities of the helix 10, helical rim 11, and scaphal area 12. The feet can be placed in any location on the exposed adhesive surface 24, such that the scaphal mold 55 of the ear molding device 29 is placed in an area of the scaphoid fossa to maintain and mold the scaphal fossa, helical rim, and helix in a substantially correct anatomic shape.

Legs 51 and 52 along with feet 53 and 54 form a curvature on their inner surface (facing the scaphal mold) configured to mold the helix to a substantially correct anatomic shape, and allow the helix and helical rim to grow along the curvature conforming to a substantially correct anatomic shape. Malleable supports 61 and 62 provide a further support structure to ear molding device 29, allowing the curvature of the legs to be adjusted to maintain the scaphal mold and/or the inside curvature of the legs in a desired position to correct deformities of the helix, helical rim, and scaphal area. In some implementations, the outer surface of legs 51 and 52 are attached to malleable supports 61 and 62, respectively. In other implementations, the malleable supports can be in other positions with respect to the legs, such as inside of the legs rather than on the outside of the legs. Malleable supports 61 and 62 can be connected to malleable retainer 60, allowing for adjustment of the ear molding device in all three dimensions.

Horizontal support 63 and 64 have an outer surface that is configured to be contacted by the cradle cover 22 when the cover is engaged with the cradle base 21. The horizontal supports 63 and 64 can reversibly engage or contact the cover when the cover is engaged with the cradle base, and when the cover is removed from the cradle base the horizontal support structures disengage from the cover. The contact between the surfaces of horizontal supports 63 and 64 and the cradle cover 22 provides an additional stability to the ear molding device resisting the traction exerted by the ear on the ear molding device and deformation of the shape of the ear molding device. If the malleable supports 61 and 62 are positioned on the outside surface of the legs 51 and 52, then the malleable support have a surface that contacts the cradle cover 22. In some implementations, the horizontal supports 63 and 64 do not contact cradle cover 22.

As discussed above, ear molding device 29 can also contact the cradle wall 34, if desired. Vertical supports 65 and 66 have an outer surface that is configured to be contacted by the cradle wall 34. When the outer surfaces of vertical supports 65 and 66 are placed in contact with the cradle wall 34, adhesive strip 35 can be used to adhere the surfaces 65 and 66 to the cradle wall 34, with or without the use of shims depending on the size of the ear being corrected. In some implementations, the ear molding device can provide tension or traction on the skin and cartilage of the area of the helix and scaphoid fossa, promoting the growth of the skin and cartilage in this area.

In some implementations, the ear molding device 29 is positioned and maintained in position by the securement provided by the feet. In other implementations, contact with one or both of the cradle cover 22 and cradle wall 34 provide support to the ear molding device 29 when in use. In some implementations, the contact with the anterior surface 31, the cradle wall 34 and the cradle cover 32 combine to maintain the shape and position of the ear molding device with respect to the forces exerted by the ear during the molding process.

The malleable retainer 60, right malleable support 61, and left malleable support 62 can be made from any malleable material, such as aluminum, copper, or silver. In other implementation, the ear molding device 29 can be dimensioned in different configurations of sizes and shapes without the malleable materials, such that a size and shape is selected that will provide the desired (substantially anatomically correct) molding characteristics for any deformities of the helix, helical rim, and the scaphoid fossa without having to shape the ear molding device to the desired configuration using the malleable retainer 60, the right malleable support 61, and the left malleable support 62.

System 100 is used to correct deformities of the ear involving the helix, antihelix, helical rim, and/or scaphoid fossa, such as cup ear, lop ear, Stahl's ear, helical rim compression/irregularities, and deformities in which there is a deficiency of skin and/or cartilage, such as Tanzer I and Tanzer II. As shown in FIG. 8, a system for correcting deformities of the ear includes assessing 802 the ear to determine if there are any deformities of the antihelix, superior crus, scaphoid fossa, helix, and/or helical rim. After determining 803 which deformities of the ear are present, selection 804 of an appropriately sized cradle and ear molding device can be made. If present, the adhesive cover 36 can be removed from the posterior adhesive surface 25 of the adhesive backing 23 positioned on the posterior surface of the cradle base 21 prior to positioning the cradle about the ear. The cradle base 21 is placed 805 around the ear 1 by passing the ear through the first opening 27 of cradle base 21. The cradle base 21 is positioned 806 such that the stint 33, if necessary, is located in an area of the posterior aspect of the ear to correct a deformed or missing (or misshaped) antihelix 14/superior crus 17. Using the stint 33, the antihelix/superior crus can be molded to the substantially correct anatomic shape. When the cradle is in the correct position, the cradle base 21 is secured 807 in position by adhering the posterior adhesive surface to the skin surrounding the base 3 of the ear, including the retroauricular skin surface 18.

The molding device 29 is shaped 808 for positioning over the helical rim 11 in the area of the scaphoid fossa. A determination 809 is made as to whether the skin and/or cartilage needs to be expanded (discussed below). If the skin and/or cartilage need to be expanded, glue is applied 810 to selected areas of the ear to be placed in contact with the ear molding device 29. Then after the glue has been applied, or if no glue is necessary, the ear molding device 29 is placed 811 over the helical rim, such that the scaphal mold 55 of the ear molding device 29 is positioned in an area of the scaphoid fossa identified to correct deformities of the helix, helical rim, and scaphoid fossa, and such that the helix and the helical rim are positioned in the space defined between the scaphal mold 55 and the legs 51 and 52. A cover over the anterior adhesive surface, if present, can be removed. The ear can be advanced 812 over the stint 33, and the right foot 53 and left foot 54 can be adhered or secured to the exposed anterior adhesive surface 24, along with an area of skin on the posterior aspect 2 of the ear being rolled out over the anterior adhesive surface, as the ear molding device is fixed in place. In some implementations, a patch of double adhesive can be used, if there is not a second opening that exposes an anterior adhesive surface. As positioned, the helix rest along the curve created by the feet 53 and 54 and the inner surface of the legs 51 and 52, defining a substantially correct anatomic curvature for the development of the helix and helical rim as the ear grows. The cradle cover 22 can then be applied 813 to the cradle base.

For ears having a deficiency of skin and/or cartilage, the ear molding device 29 can be used to grip the helical rim and expand the dimensions of the ear in the area of the inner surface of the helical rim and the scaphoid fossa by putting a lateral force on the ear pulling the ear out to expand the cartilage and skin. Expansion of the skin and cartilage can be used to correct deformities such as Tanzer I and II, which appear like lop ear, but there have a deficiency of skin (Tanzer I and II) and cartilage (Tanzer II) on the inner surface of the helix and the helical rim that prohibits rolling the rim out.

To grip the helical rim and apply tension to the ear, a bonding agent can be used, such as medically approved glue, for example cyanomethacrylate or cyanoacrylate. The bonding agent can be applied selectively to portions of the ear which are placed in contact with the ear molding device 29 to maintain tension and prevent the ear from slipping out of the ear molding device. The ear molding device 29 can be adhered to anterior adhesive surface and to the inner wall 34 of the cradle base 21 proximate to the ear molding device in order to more firmly fix the ear molding device in place to resist any opposing tension generated by the ear.

After positioning the cradle base 21 around the ear, and positioning the scaphal mold 55 of the ear molding device 29 in the scaphoid fossa, and fixedly securing the feet to the anterior adhesive surface, the cradle cover 22 is engaged with the cradle base 21. As discussed above, the cradle cover 22 can be positioned in contact with the horizontal support surfaces of the legs, providing additional support to maintain both the shape and the fixed position of the ear molding device. This additional support provided by the cradle cover 22 helps to prevent deformation of the ear molding device and possible movement caused by the tension exerted by the ear. Thus, the design of the cradle and the ear molding device complement each other to create a additive reinforcement of both the shape of the ear molding device, and the fixed positioning of the ear molding device after placement. Additionally, this helps maintain tension provided by the ear molding device on the ear in the area of the helix, helical rim and scaphoid fossa.

When correcting the shape of the misshaped ear, the duration of treatment with the above described system depends on the age of the infant or neonate at the time of diagnosis. An earlier diagnosis can shorten the duration of treatment. For example, when treatment begins at about 1 week of age, the duration of the treatment may be in the range of 6 to 8 weeks. However, if the diagnosis is not made until 3 weeks of age, then the duration of treatment may be in the range of 4 to 6 months. It may be necessary in cases where the cartilage and skin need to be expanded to repeat the process two or three times in order to achieve the necessary growth of the skin and cartilage and mold the ear to a substantially correct anatomic shape.

A number of implementations have been described. Nevertheless, it will be understood that various modifications may be made. For example, the size and shape of various components may be altered and different material may be used to make the various components. Different ways to secure the components in their desired positions can be used. Accordingly, other implementations are within the scope of the following claims.

What is claimed is:

1. A method of correcting a misshaped ear, wherein the ear includes an antihelix, a superior limb of the triangular fossa, a helix, a helical rim, a base, a concha, and a scaphal area, the method comprising:

placing a cradle base over the ear, wherein the cradle base includes an anterior surface, a posterior surface, and an opening dimensioned to accommodate passage of the ear, and wherein the cradle base is releasably engageable with a cradle cover to define a compartment between an inner surface of the cover and the anterior surface of the base, such that the ear is positioned within the compartment;

locating a splint on the anterior surface, such that the splint is arranged on the anterior surface in a position substantially corresponding to an area of the antihelix and the superior limb of the triangular fossa;

placing a posterior surface of the ear between the base of the ear and the helical rim over the splint, such that the splint maintains a substantially correct anatomical configuration of the ear in the area of the antihelix and the superior limb of the triangular fossa; and retaining the helix in a space defined between a scaphal mold and one or more braces supporting the scaphal mold, such that the scaphal mold maintains a substantially correct anatomical configuration of the scaphal area of the ear.

2. The method of claim 1 comprising securing the one or more braces to the anterior surface.

3. The method of claim 2 comprising engaging the cradle cover with the cradle base.

\* \* \* \* \*